United States Patent [19]

Lavielle et al.

[11] Patent Number: 5,500,443

[45] Date of Patent: Mar. 19, 1996

[54] NEW BENZODIOXANE COMPOUNDS

[75] Inventors: Gilbert Lavielle, La Celle Saint Cloud; Patrick Hautefaye, Servon Brie Comte Robert; Olivier Muller, Ennery; Mark Millan; Mauricette Brocco, both of Paris, all of France

[73] Assignee: Adir et Compagnie, Courbevoie, France

[21] Appl. No.: 392,203

[22] Filed: Feb. 22, 1995

[30] Foreign Application Priority Data

Feb. 25, 1994 [FR] France .................... 94 02161

[51] Int. Cl.⁶ ................. C07D 207/04
[52] U.S. Cl. ............ 514/422; 514/212; 514/321; 514/359; 514/379; 514/393; 514/394; 514/452; 548/241; 548/311.7; 548/361.1; 548/574; 548/575; 546/197; 549/362; 549/366; 540/596
[58] Field of Search ............ 549/366, 362; 514/452, 422, 321, 393, 394, 379, 359, 212; 548/574, 575, 311.7, 241, 361.1; 546/197; 540/596

[56] References Cited

PUBLICATIONS

CA 72:55353j Synthesis of . . . –1,4–benzodioxan, Dauksas et al., p. 422, 1970.

*Primary Examiner*—Joseph K. McKane
*Attorney, Agent, or Firm*—The Firm of Gordon W. Hueschen

[57] ABSTRACT

A compound of formula (I):

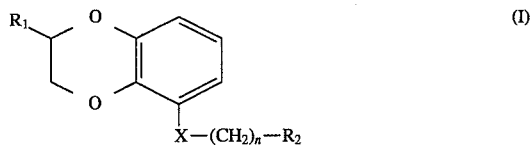

in which:

X represents oxygen or methylene, n represents 1, 2 or 3, $R_1$ represents hydrogen, aminocarbonyl or hydroxymethyl, $R_2$ represents:

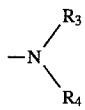

in which $R_3$ and $R_4$ are as defined in the description, the isomers thereof and the addition salts thereof with a pharmaceutically acceptable acid or base, and medicinal products containing the same are useful in the treatment of schizophrenia.

8 Claims, No Drawings

NEW BENZODIOXANE COMPOUNDS

FIELD OF THE INVENTION

The present invention relates to new benzodioxane compounds.

DESCRIPTION OF THE PRIOR ART

A certain number of 1,4-benzodioxane derivatives have been described in the literature. This is more particularly the case for the compounds described in Patents EP 307,970, EP 210,581 or FR 2,449,088, which exhibit a vasodilatory activity or alternatively for the compounds described in Patent EP 446,921, which possess anxiolytic properties.

SUMMARY OF THE INVENTION

Besides the fact that they are novel, the compounds of the present invention exhibit particularly advantageous pharmacological properties. Indeed, one of the challenges in psychopharmacology today is to find novel medicaments which allow better control of schizophrenia, the treatment of which is currently unsatisfactory. Conventional neuroleptic agents, such as haloperidol, provide quite good care for the productive symptoms (such as fabulation and hallucinations) but their effectiveness with regard to deficiency symptoms (such as social withdrawal) is very poor. Furthermore, they induce an extrapyramidal syndrome of Parkinson type, as has been indicated by A. Y. Deutch et al. (Schizophrenia Research, 4, 121–151, 1991) and H. Y. Meltzer et al. (Pharmacol. Rev., 43,587–604, 1991).

Unlike haloperidol, clozapine is more effective in treating the deficiency symptoms, and it is even effective in patients who are resistant to haloperidol. Moreover, it appears not to bring about an extrapyramidal syndrom, as has been indicated by Coward et at. (Psychopharmacology, 99, s6–s12, 1989). This difference is apparently due to the receptor profile of clozapine, which differs from that of haloperidol: for example, its low relative activity on the $D_2$ receptors and its relatively high affinity for the adrenergic ($\alpha_1$) and serotinergic (5-$HT_{2A}$; 5-$HT_{2C}$) receptors. These results have been indicated by H. Canton et al. (Eur. J. Pharmacol., 191, 93–96, 1990) as well as by A. Y. Deutch and H. Y. Meltzer, cited above.

Moreover, unlike haloperidol, clozapine shows a certain affinity for the 5-$HT_{1A}$ receptors, the activation of which is associated with anxiolytic, antidepressant and possibly even antipsychotic effects, as has been indicated by S. Ahlenius (Pharmacol. & Toxicol., 64, 3–5, 1989), J. E. Barrett et al. (in "5-$HT_{1A}$ agonists, 5-$HT_3$ antagonists and benzodiazepines: their comparative behavioural pharmacology" Ed. R. J. Rogers and S. J. Cooper, Wiley & Sons Ltd., Chichester, pp. 59–105, 1991), M. J. Millan et al. (Drug News & Perspectives, 5, 397–466, 1992), J. M. A. Sitsen (Drug News & Perspectives, 4, 414–418, 1991).

However, on account of its toxicity, clozapine cannot be envisaged in the general treatment of schizophrenic states. It was thus particularly advantageous to find products sharing the mechanism of clopazine but devoid of its toxic effects, which are directly associated with its specific chemical structure.

The compounds described in this patent correspond to the desired profile. Indeed, they exhibit (in vitro and in vivo) a very similar biochemical and functional profile to that of clopazine and, in addition, have higher affinities for the 5-$HT_{1A}$ receptors. They thus possess an original profile which appears to be well suited to a better treatment of schizophrenia, in comparison with that which may currently be obtained with the products available.

DETAILED DESCRIPTION OF THE INVENTION

More specifically, the present invention relates to the compounds of formula (I):

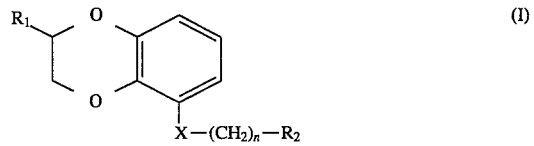

in which:

X represents an oxygen atom or a methylene group, n represents 1, 2 or 3, $R_1$ represents a hydrogen atom, an aminocarbonyl group or a hydroxymethyl group, $R_2$ represents a group:

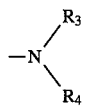

in which:

either $R_3$ represents a hydrogen atom or a linear or branched ($C_1$–$C_6$) alkyl group, and $R_4$ represents:
a linear or branched ($C_1$–$C_4$) alkyl group
which is unsubstituted or substituted with a phenyl group (which may or may not be substituted with one or more halogen atoms or linear or branched ($C_1$–$C_4$) alkyl groups, linear or branched ($C_1$–$C_4$) alkoxy groups, trihalomethyl groups or hydroxyl groups), on condition that, in these cases, $R_1$ is other than a hydrogen atom,
or which is substituted with a benzoylamino group (which may or may not be substituted on the phenyl ring with one or more halogen atoms or linear or branched ($C_1$–$C_4$) alkyl groups, linear or branched ($C_1$–$C_4$) alkoxy groups, trihalomethyl groups or hydroxyl groups),
or a benzoyl group (which may or may not be substituted with one or more halogen atoms or linear or branched ($C_1$–$C_4$) alkyl groups, linear or branched ($C_1$–$C_4$) alkoxy groups, trihalomethyl groups or hydroxyl groups).

or $R_3$ and $R_4$ form, together with the nitrogen atom to which they are attached, a group:

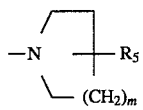

in which:

m represents 1, 2 or 3, $R_5$ represents a benzoyl (which may or may not be substituted with one or more halogen atoms or linear or branched ($C_1$–$C_4$) alkyl groups, linear or branched ($C_1$–$C_4$) alkoxy groups, hydroxyl groups or trihalomethyl groups), benzoylmethyl (which may or may not be substituted on the phenyl ring with one or more halogen atoms or linear or branched ($C_1$–$C_4$) alkyl groups, linear or branched ($C_1$–$C_4$) alkoxy groups, hydroxyl groups or trihalomethyl groups), 2-oxo-(3H)-benzimidazol-1-yl, 1H-indazol-3-yl methyl (which may or may not be substituted on the phenyl ring with a halogen atom), or 1,2-benzisoxazol-3-yl methyl group (which may or may not be substituted on the phenyl ring with a halogen atom), the enantiomers, diastereoisomers and epimers thereof, and the addition salts thereof with a pharmaceutically acceptable acid or base.

Among the pharmaceutically acceptable acids which may be mentioned, without any limitation being implied, are hydrochloric acid, hydrobromic acid, sulfuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulfonic acid, camphoric acid, etc.

Among the pharmaceutically acceptable bases which may be mentioned, without any limitation being implied, are sodium hydroxide, potassium hydroxide, triethylamine, tert-butylamine, etc.

The invention also covers the process for the preparation of the compounds of formula (I).

The process for the preparation of the compounds of formula (I), such that X represents an oxygen atom and $R_1$ represents a hydrogen atom, comprises a compound of formula (II) being used as starting material:

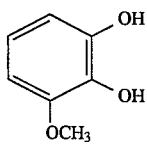
(II)

which compound is reacted with 1,2-dibromoethane in the presence of potassium carbonate and copper powder in an alcoholic medium, to give the compound of formula (III):

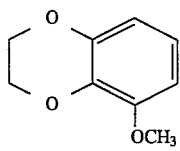
(III)

which compound is converted, in an acidic medium, into the compound of formula (IV):

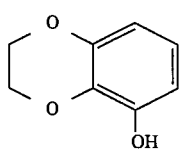
(IV)

which compound of formula (IV) is condensed: either with a compound of formula (V), after reacting with sodium ethoxide:

Br—(CH$_2$)$_n$—Cl (V)

in which n has the same meaning as in the formula (I), to give the compound of formula (VI):

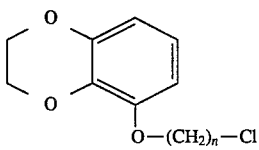
(VI)

in which n has the same meaning as in the formula (I), which compound is then reacted with an amine of formula (VII), the isomers of which have optionally been separated:

(VII)

in which $R'_4$ has the same meaning as $R_4$ except for the case where $R_4$ represents a substituted or unsubstituted benzoyl group, to give the compound of formula (I/a), a specific case of the compounds of formula (I):

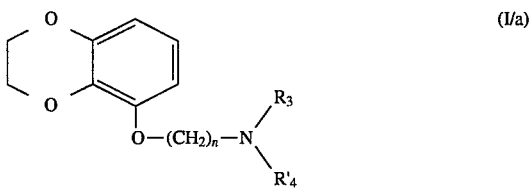
(I/a)

in which n, $R_3$ and $R'_4$ have the same meaning as above, or with a nitrile of formula (VIII), in a basic medium,

Br—(CH$_2$)$_{n-1}$—CN (VIII)

in which n has the same meaning as in the formula (I), to give the compound of formula (IX):

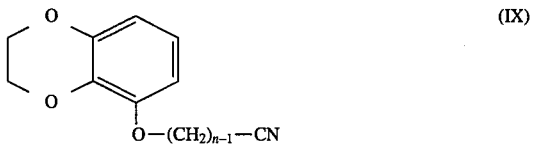
(IX)

in which n has the same meaning as in the formula (I), which compound is reduced using lithium aluminum hydride, to give the compound of formula (X):

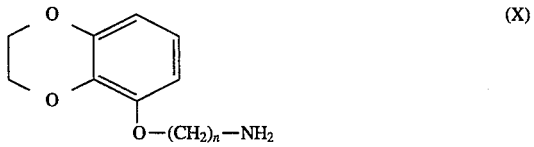
(X)

in which n has the same meaning as in the formula (I), which compound is reacted with an acid chloride of formula (XI):

Cl—CO—R''$_4$ (XI)

in which R''$_4$ represents a phenyl group (which may or may not be substituted with one or more halogen atoms or linear or branched ($C_1$–$C_4$) alkyl groups, linear or branched ($C_1$–$C_4$) alkoxy groups, trihalomethyl groups or hydroxyl groups), to give the compound of formula (I/b), a specific case of the compounds of formula (I):

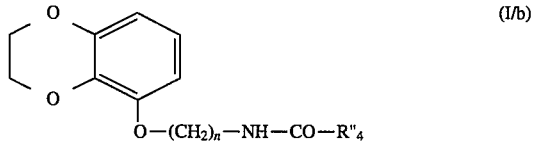
(I/b)

in which n and R''$_4$ have the same meaning as above, which compound of formula (I/b) may, if so desired, undergo a reduction in the presence of tetrabutylammonium borohydride, to give the compound of formula (I/c), a specific case of the compounds of formula (I):

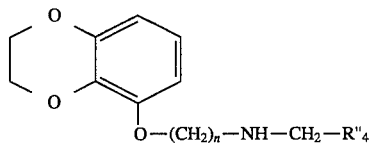

in which n and $R''_4$ have the same meaning as above, which compound of formula (I/a), (I/b) or (I/c):
- may be purified, if required, according to a standard purification technique, and
- the isomers of which are, if required, separated according to a standard separation technique, and
- which is converted, if so desired, into the addition salts thereof with a pharmaceutically acceptable base.

The process for the preparation of the compounds of formula (I), such that X represents an oxygen atom and $R_1$ represents an aminocarbonyl or hydroxymethyl group, comprises a compound of formula (XII) being used as starting material:

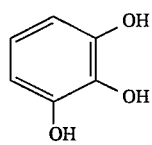

which compound is reacted with ethyl 2,3-dibromopropionate, in a basic medium, to give the compound of formula (XIII):

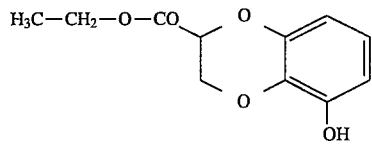

which compound is reacted, if so desired, in an ammoniacal solution, to give the compound of formula (XIV):

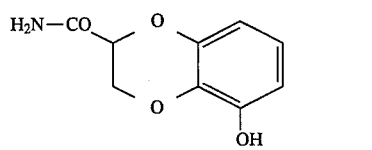

which compound of formula (XIII) or (XIV) is condensed: either with a compound of formula (V):

in which n has the same meaning as in the formula (I), to give the compounds of formula (XV) or (XVI) respectively:

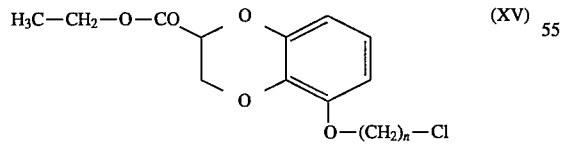

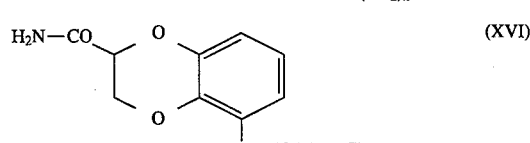

in which n has the same meaning as in the formula (I), which compounds are reacted respectively with an amine of formula (VII), the isomers of which have optionally been separated:

in which $R'_4$ has the same meaning as $R_4$, except for the case where $R_4$ represents a substituted or unsubstituted benzoyl group, to give the compounds of formula (XVII) or (I/d), a specific case of the compounds of formula (I):

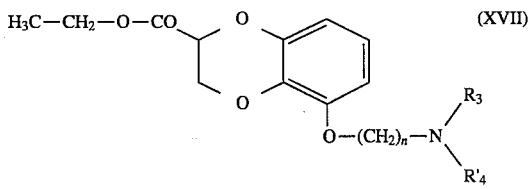

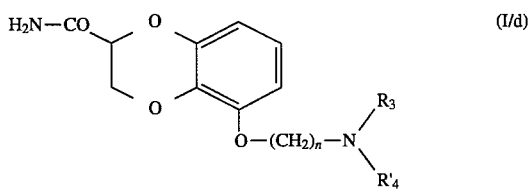

in which n, $R_3$ and $R'_4$ have the same meaning as above, which compound of formula (XVII) is reduced in the presence of lithium aluminum hydride, to give the compound of formula (I/e), a specific case of the compounds of formula (I):

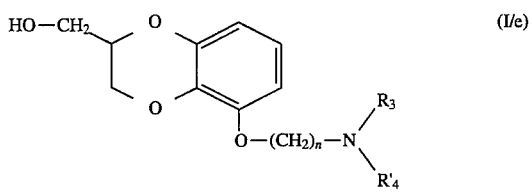

in which n, $R_3$ and $R'_4$ have the same meaning as in the formula (I), or with a nitrile of formula (VIII), in a basic medium,

in which n has the same meaning as in the formula (I), to give the compounds of formula (XVIII) or (XIX) respectively:

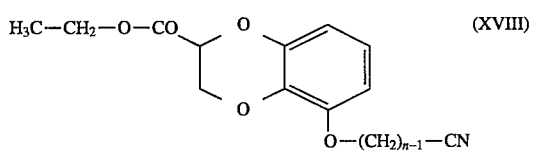

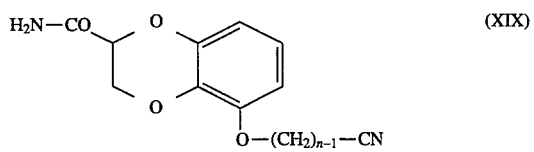

in which n has the same meaning as in the formula (I), which compounds are reduced using lithium aluminum hydride, to give the compounds of formula (XX) or (XXI) respectively:

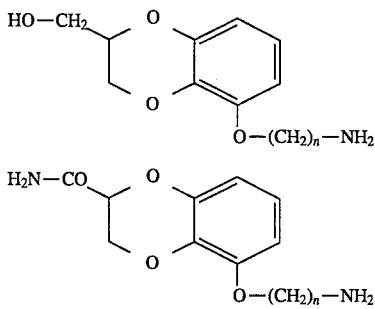
(XX)

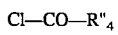
(XXI)

in which n has the same meaning as in the formula (I), which compounds are reacted, respectively, with an acid chloride of formula (XI):

Cl—CO—R"₄ (XI)

in which R"₄ represents a phenyl group (which may or may not be substituted with one or more halogen atoms or linear or branched ($C_1$-$C_4$) alkyl groups, linear or branched ($C_1$-$C_4$) alkoxy groups, trihalomethyl groups or hydroxyl groups), to give the compounds of formula (I/f) or (I/g) respectively, specific cases of the compounds of formula (I):

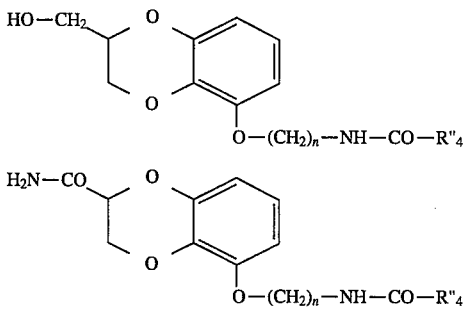
(I/f)

(I/g)

in which n and R"₄ have the same meaning as above, which compounds of formula (I/f) or (I/g) may, if so desired, undergo a reduction in the presence of tetrabutylammonium borohydride, to give the compounds of formula (I/h) or (I/i) respectively, specific cases of the compounds of formula (I):

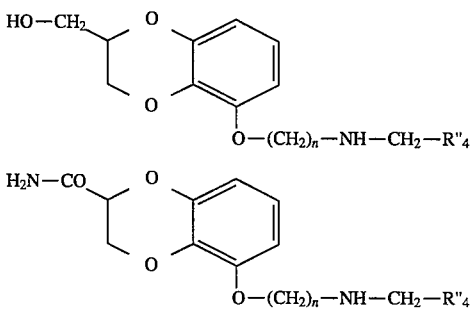
(I/h)

(I/i)

in which n and R"₄ have the same meaning as above, which compound of formula (I/d), (I/e), (I/f), (I/g), (I/h) or (I/i):

- may be purified, if required, according to a standard purification technique, and
- the isomers of which are, if required, separated according to a standard separation technique, and
- which is converted, if so desired, into the salts thereof with a pharmaceutically acceptable base.

The process for the preparation of the compounds of formula (I), such that X represents a methylene group, comprises a compound of formula (XXII) (obtained from 2,3-dihydroxybenzaldehyde according to the process described in J. Med. Chem., 26, 193, 1989) being used as starting material:

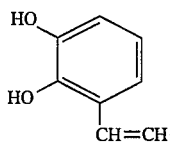
(XXII)

in which n has the same meaning as in the formula (I), which undergoes a catalytic hydrogenation to give the compound of formula (XXIII):

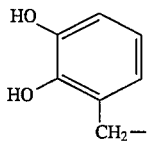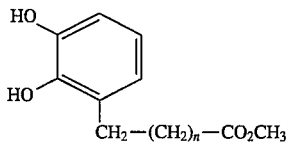
(XXIII)

in which n has the same meaning as in the formula (I), which compound is reduced in the presence of lithium aluminum hydride, to give the compound of formula (XXIV):

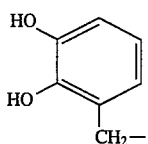
(XXIV)

in which n has the same meaning as in the formula (I), which compound is reacted with 1,2-dibromoethane or with ethyl 2,3-dibromopropionate, depending on the derivative of formula (I) which it is desired to obtain, to give the compound of formula (XXV):

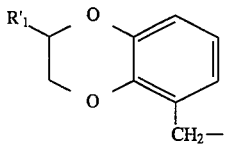
(XXV)

in which R'₁ represents a hydrogen atom or an ethoxycarbonyl group, which compound of formula (XXV) (which, when R'₁ represents an ethoxycarbonyl group, may, if so desired, be subjected to the action of an ammoniacal solution, to give the corresponding amide), is then reacted with carbon tetrabromide in the presence of triphenylphosphine, to give the compound of formula (XXVI),

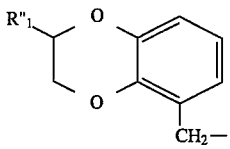
(XXVI)

in which n has the same meaning as in the formula (I), and R"₁ represents a hydrogen atom or an ethoxycarbonyl or aminocarbonyl group, which compound is then reacted with an amine of formula (VII), the isomers of which have optionally been separated:

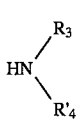
(VII)

in which R'₄ has the same meaning as R₄, except for the case where R₄ represents a substituted or unsubstituted benzoyl group, to give the compound of formula (I/j), a specific case of the compounds of formula (I) (after conversion, in the presence of lithium aluminum hydride, of the group R"₁, when it represents an ethoxycarbonyl group, into a hydroxymethyl group):

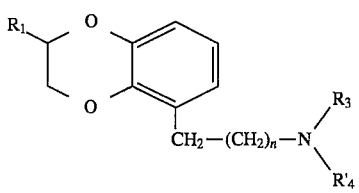

in which $R_1$, n, $R_3$ and $R'_4$ have the same meaning as above, which compound of formula (I/j):

may, if required, be purified according to a standard purification technique, and the isomers of which are separated, if required, according to a standard separation technique, and which is converted, if so desired, into the addition salts thereof with a pharmaceutically acceptable base.

The subject of the present invention is also the pharmaceutical compositions containing, as active principle, at least one compound of formula (I), alone or in combination with one or more inert, non-toxic vehicles or excipients.

Among the pharmaceutical compositions according to the invention, there may more particularly be mentioned those which are suitable for oral, parenteral or nasal administration, simple or coated tablets, sublingual tablets, gelatin capsules, lozenges, suppositories, creams, ointments, dermal gels, etc.

The useful dosage varies depending on the age and weight of the patient, the nature and severity of the complaint, and the route of administration. The latter may be oral, nasal, rectal or parenteral. Generally speaking, the unit dosage ranges between 20 μg and 2 mg for a treatment dose taken 1 to 3 times per 24 hours.

The examples which follow illustrate the invention and in no way imply a limitation thereof.

The starting materials used are known products or are prepared according to known procedures.

Preparations A, B and C do not lead to the compounds of the invention, but to synthesis intermediates which are useful in the preparation of the compounds of formula (I).

Preparation A: N-Propyl-N-[2-(4-fluorobenzoylamino)ethyl]amine

Stage A: N-(2-Bromoethyl)-4-fluorobenzamide

To a suspension containing 0.23 mol of-bromoethylamine hydrobromide in 200 ml of chloroform, stirred at 5° C., is added dropwise a solution containing 0.21 mol of 4-fluorobenzoyl chloride in 50 ml of chloroform, followed by a solution containing 0.46 mol of triethylamine in 100 ml of chloroform. The mixture is then stirred at room temperature for 1 hour and then at reflux for 4 hours. After cooling and evaporation of the solvent, the residue is taken up in 200 ml of ether. After filtration of the salts and concentration of the solvent, the expected product is obtained by purification of the residue by chromatography on a column of silica, using a dichloromethane/acetone (98/2) mixture as eluent.

Stage B: N-Propyl-N-[2-(4-fluorobenzoylamino)ethyl]amine

The product obtained in the preceding stage, dissolved in 40 ml of propylamine, is maintained at reflux for 4 hours. After cooling and distillation of the excess propylamine, the expected product is obtained after purification by chromatography on a column of silica, using a dichloromethane/methanol/aqueous ammonia (90/10/1) mixture as eluent.

Preparation B: 3-[(6-Fluoro-1,2-benzisoxazol-3-yl)methyl]pyrrolidine

Stage A: 1-Benzyl-3-[2-(2,4-difluorophenyl)-2-hydroxyethyl]pyrrolidine

A solution containing 0.38 mol of 1-benzyl-3-chloromethylpyrrolidine in 200 ml of tetrahydrofuran (THF) is added, at 65° C., to a suspension containing 9.3 g of magnesium in 100 ml of THF. The mixture is maintained at reflux and, after disappearance of the metal, followed by cooling, this solution is added to a solution containing 0.38 mol of 2,4-difluorobenzaldehyde in 300 ml of THF. The mixture is maintained at room temperature for 12 hours and is then hydrolyzed with 220 ml of saturated ammonium chloride solution. After extraction with dichloromethane and then evaporation, the residual oil is purified by chromatography on a column of silica, using a dichloromethane/methanol/aqueous ammonia (98/2/0.2) mixture as eluent, and gives the expected product.

Stage B: 1-Benzyl-3-(2,4-difluorobenzoylmethyl)pyrrolidine 67 g of chromium trioxide are added, with stirring and at 0° C., to 700 ml of pyridine, followed, 15 minutes later, by 0.214 mol of the compound described in the preceding stage, dissolved in 150 ml of pyridine. The mixture is maintained at room temperature for 12 hours, evaporated and the residue is taken up in 500 ml of water and 500 ml of dichloromethane. The precipitate formed is filtered off and washed with dichloromethane. The organic phases are combined, washed with 1N sodium hydroxide, with saturated sodium chloride solution and then dried and evaporated. The residual oil is purified by chromatography on a column of silica, using a dichloromethane/methanol/aqueous ammonia (98/2/0.2) mixture as eluent, and gives the expected product.

Stage C: 1-Benzyl-3-[6-fluoro-1,2-benzisoxazol-3-yl)methyl]pyrrolidine 0.19 tool of the product obtained in the preceding stage and 0.95 mol of hydroxylamine hydrochloride in 600 ml of pyridine are maintained at reflux for 24 hours. After concentration of the solvent, the residue is taken up in dichloromethane. The organic phase is then washed with water and evaporated. The residue is taken up in 100 ml of dimethylformamide (DMF) and is added to a suspension containing 4.3 g of sodium hydride in 50 ml of DMF. After stirring for one hour, the reaction mixture is hydrolyzed and then extracted with dichloromethane. After washing the organic phase with water and evaporation of the solvent, the residual oil is purified by chromatography on a column of silica, using a dichloromethane/methanol (97/3) mixture as eluent, and gives the expected product.

Stage D: 1-Ethoxycarbonyl-3-[6-fluoro-1,2-benzisoxazol-3-yl)methyl]pyrrolidine

A mixture containing 80 mmol of the compound obtained in the preceding stage and 160 mmol of ethyl chloroformate in 350 ml of toluene is maintained at reflux for 24 hours. After cooling, washing of the toluene phase with 1N hydrochloric acid, then with 1N sodium hydroxide and evaporation, the expected product is obtained.

Stage E: 3-[(6-Fluoro-1,2-benzisoxazol-3-yl)methyl]pyrrolidine 58 mmol of the compound obtained in the preceding stage and 250 ml of 48% hydrobromic acid are heated at 90° C. for 1 hour. After concentration, the expected product is obtained by release from the residue using 5N sodium hydroxide.

Preparation C: 3-[(6-Fluoro-1H-indazol-3-yl)methyl]pyrrolidine

Stage A: 1-Benzyl-[(6-Fluoro-1H-indazol-3-yl)methyl]pyrrolidine 64 mmol of the compound obtained in Stage B of Preparation B and 64 mmol of hydrazine hydrate in 200 ml of 1-butanol are maintained at reflux for 72 hours. After cooling and evaporation, the residue is taken up in dichloromethane. The organic phase is washed with water and evaporated. The residual oil is purified by chromatography on a column of silica, using a dichloromethane/methanol/aqueous ammonia (96/4/0.4) mixture as eluent.

Stage B: 3-[(6-Fluoro-1H-indazol-3-yl)methyl]pyrrolidine

The product obtained in the preceding stage undergoes a catalytic debenzylation in ethanol, at 45° C., using 10% palladium on charcoal as catalyst.

EXAMPLE 1

5-{2-[4-(4-Fluorobenzoyl)piperidino]ethoxy}-1,4-benzodioxane hydrochloride

Stage A: 5-Methoxy-1,4-benzodioxane

A heterogeneous mixture containing 1.42 mol of 3-methoxycatechol, 1.57 mol of 1,2-dibromoethane, 1.42 mol of potassium carbonate and 4 g of copper powder in 150 ml of glycerol is heated at 110° C. for 15 hours. After cooling, the mixture is poured into 1 l of water. The aqueous phase is extracted with ethyl ether. The ether phases are then washed with 1N sodium hydroxide, dried and evaporated, and give the expected product.

Stage B: 5-Hydroxy-1,4-benzodioxane

The compound obtained in the preceding stage is maintained at reflux in 500 ml of 48% hydrobromic acid and 800 ml of glacial acetic acid. After cooling and concentration, the residue is taken up in 1 l of water and the aqueous phase is extracted with ethyl ether. The ether phases are combined and evaporated. The expected product is obtained after purification by chromatography on a column of silica, using dichloromethane as eluent.

Stage C: 5-(2-Chloroethoxy)-1,4-benzodioxane

To 500 ml of 1N sodium ethoxide solution is added dropwise a solution containing 500 mmol of the compound obtained in the preceding stage in 150 ml of ethanol. The mixture is stirred for 1 hour, and a solution containing 500 mmol of 1-bromo-2-chloroethane in 150 ml of ethanol is added to the above mixture. The mixture is then maintained at reflux for 24 hours. After cooling, filtration of the salts and evaporation, the residue is taken up in isopropyl ether and the expected product which precipitates is filtered off. Melting point: 73° C.

Stage D: 5-{2-[4-(4-Fluorobenzoyl)piperidino]ethoxy}-1,4-benzodioxane hydrochloride A mixture containing 21 mmol of the product obtained in the preceding stage, 17 mmol of 4-(4-fluorobenzyl)piperidine, 21 mmol of potassium carbonate and a few mg of potassium iodide in 50 ml of 4-methyl-2-pentanone is maintained at reflux for 18 hours. After cooling, 50 ml of water are added to the reaction medium and the aqueous phase is extracted with dichloromethane. The organic phases are combined, washed, dried and evaporated. The expected product, in the form of the base, is obtained after purification of the residue by chromatography on a column of silica, using a dichloromethane/ethanol (98/2) mixture as eluent. It is converted into the corresponding hydrochloride by dilution in ethyl ether and dropwise addition of the stoichiometric amount of 10N hydrochloric ethanol. The hydrochloride is then filtered off, washed with ether and dried. Melting point: 152° C.

| | Elemental microanalysis: | | | |
|---|---|---|---|---|
| | C % | H % | N % | Cl % |
| calculated | 62.63 | 5.97 | 3.32 | 8.40 |
| found | 62.49 | 5.95 | 3.18 | 8.47 |

The products of Examples 2 to 8 were prepared according to the process described in Example 1, using the corresponding starting materials.

EXAMPLE 2

5-{2-[3-(4-Fluorobenzoylmethyl)pyrrolidin-1-yl}-1,4-benzodioxane hydrochloride

Stages A, B, C: identical to Stages A, B and C of Example 1.

Stage D: Replace 4-(4-fluorobenzoyl)piperidine with 3-(4-fluorobenzylmethyl)pyrrolidine.

Melting point: 134° C.

| | Elemental microanalysis: | | | |
|---|---|---|---|---|
| | C % | H % | N % | Cl % |
| calculated | 62.63 | 5.97 | 3.32 | 8.40 |
| found | 62.64 | 6.06 | 3.16 | 8.52 |

EXAMPLE 3

5-{2-[4-(2-Oxo-(3H)-benzimidazol-1-yl)piperidino]ethoxy}-1,4-benzodioxane hydrochloride Stages A, B, C: identical to Stages A, B and C of Example 1.

Stage D: Replace 4-(4-fluorobenzoyl)piperidine with 1-(piperidin-4-yl)-2-(3H)-benzimidazolone.

Melting point: 155° C.

| | Elemental microanalysis: | | | |
|---|---|---|---|---|
| | C % | H % | N % | Cl % |
| calculated | 61.18 | 6.07 | 9.73 | 8.21 |
| found | 61.07 | 6.1 | 9.71 | 8.14 |

EXAMPLE 4

5-{2-[N-propyl-N-[2-(4-Fluorobenzoylamino)ethyl] amino]ethoxy}-1,4-benzodioxane hydrochloride Stages A, B, C: identical to stages A, B and C of Example 1.

Stage D: Replace 4-(4-fluorobenzoyl)piperidine with the amine described in Preparation A.

Melting point: 147° C.

| | Elemental microanalysis: | | | |
|---|---|---|---|---|
| | C % | H % | N % | Cl % |
| calculated | 60.20 | 6.43 | 6.38 | 8.08 |
| found | 59.71 | 6.53 | 6.33 | 8.27 |

EXAMPLE 5

5-{2-[3-(4-Fluorobenzoylmethyl)pyrrolidin-1-yl]ethoxy}-1,4-benzodioxane hydrochloride, (+) isomer Stages A, B, C: identical to Stages A, B and C of Example 1.

Stage D: Replace 4-(4-fluorobenzoyl)piperidine with the (+) isomer of 3-(4-fluorobenzoylmethyl)pyrrolidine obtained according to the process described in Patent EP 389,352.

The hydrochloride is obtained by salification of the base in an acetone/ethyl ether (50/50) mixture with one equivalent of hydrochloric acid in ethanol. Melting point: 120°–122° C. Optical rotation: $[\alpha]_D^{21}=+4.15°$ (c=1%, methanol)

Elemental microanalysis:

|  | C % | H % | N % | Cl % |
|---|---|---|---|---|
| calculated | 62.63 | 5.97 | 3.32 | 8.40 |
| found | 62.65 | 5.89 | 3.31 | 8.41 |

EXAMPLE 6

5-{2-[3-(4-Fluorobenzoylmethyl)pyrrolidin-1-yl]ethoxy}-1,4-benzodioxane hydrochloride, (–) isomer
Stages A, B, C: identical to Stages A, B and C of Example 1.
Stage D: Replace 4-(4-fluorobenzoyl)piperidine with the (–) isomer of 3-(4-fluorobenzoylmethyl)pyrrolidine obtained according to the process described in Patent EP 389,352.

The hydrochloride is obtained as described in Example 5. Melting point: 120°–122° C. Optical rotation: $[\alpha]_D^{21}=-4.75°$ (c=1%, methanol)

Elemental microanalysis:

|  | C % | H % | N % | Cl % |
|---|---|---|---|---|
| calculated | 62.63 | 5.97 | 3.32 | 8.40 |
| found | 62.59 | 5.86 | 3.37 | 8.28 |

EXAMPLE 7

5-{2-[3-[(6-Fluoro-1H-indazol-3-yl)methyl]pyrrolidin-1-yl]ethoxy}-1,4-benzodioxane hydrochloride
Stages A, B, C: identical to Stages A, B and C of Example 1.
Stage D: Replace 4-(4-fluorobenzoyl)piperidine with 3-[(6-fluoro-1H-indazol-3-yl)methyl]pyrrolidine described in Preparation C.

Purification of the expected product, in base form, is performed by chromatography on a column of silica, using a dichloromethane/methanol/aqueous ammonia (95/5/0.5) mixture as eluent.

Elemental microanalysis:

|  | C % | H % | N % | Cl % |
|---|---|---|---|---|
| calculated | 61.26 | 5.78 | 9.75 | 7.40 |
| found | 61.33 | 6.05 | 9.14 | 7.35 |

EXAMPLE 8

5-{2-[3-[(6-Fluoro-1,2-benzisoxazol-3-yl)methyl] pyrrolidin-1-yl]ethoxy}-1,4-benzodioxane hydrochloride
Stages A, B, C: identical to Stages A, B and C of Example 1.
Stage D: Replace 4-(4-fluorobenzoyl)piperidine with 3-[(6-fluoro-1,2-benzisoxazol-3-yl)methyl]pyrrolidine described in Preparation B.

Purification of the product obtained, in base form, is performed by chromatography on a column of silica, using a dichloromethane/methanol (97/3) mixture as eluent.

Elemental microanalysis:

|  | C % | H % | N % |
|---|---|---|---|
| calculated | 60.76 | 5.56 | 6.44 |
| found | 61.21 | 5.54 | 6.49 |

EXAMPLE 9

5-{2-[4-(4-Fluorobenzoyl)piperidino]ethoxy}-1,4-benzodioxane-2-carboxamide hydrochloride
Stage A: Ethyl ester of 5-hydroxy-1,4-benzodioxane-2-carboxylic acid
To a solution containing 0.8 mol of pyrogallol in 1 l of acetate are added 2.4 mol of potassium carbonate, followed by dropwise addition of 2.4 mol of ethyl 2,3-dibromopropionate. The mixture is then maintained at reflux for 15 hours. After cooling, filtration of the precipitate and washing of the latter with acetone, the filtrate is recovered and concentrated. The residue is taken up in ether and, after filtration of the ether phase, the latter is evaporated and gives the expected product.
Stage B: 5-Hydroxy-1,4-benzodioxane-2-carboxamide
A mixture containing 350 mmol of the product obtained in the preceding stage in 1.3 l of a 28% ammoniacal solution is stirred at room temperature for 18 hours. After concentration of the reaction medium, the residue is taken up in 300 ml of ether. The expected product is obtained after filtration of the precipitate formed and is dried.
Stage C: 5-(2-Chloroethoxy)-1,4-benzodioxane-2-carboxamide
The expected product is obtained according to the process described in Stage C of Example 1, from the compound obtained in the above stage.
Stage D: 5-{2-[4-(4-Fluorobenzoyl)piperidino]ethoxy}-1,4-benzodioxane-2-carboxamide hydrochloride
The expected product is obtained according to the process described in Stage D of Example 1, from the compound described in the above stage. Melting point: 215° C.

Elemental microanalysis:

|  | C % | H % | N % | Cl % |
|---|---|---|---|---|
| calculated | 59.42 | 5.64 | 6.03 | 7.63 |
| found | 59.39 | 5.80 | 5.83 | 7.59 |

EXAMPLE 10

2-Hydroxymethyl-5-[2-(N,N-dipropylamino)ethoxy]-1,4-benzodioxane oxalate
Stage A: Ethyl ester of 5-(2-chloroethyl)-1,4-benzodioxane-2-carboxylic acid
The expected product is obtained from the compound described in Stage A of Example 9, according to the process described in Stage C of Example 1.
Stage B: Ethyl ester of 5-[2-(N,N-dipropylaminoethoxy]-1,4-benzodioxane-2-carboxylic acid
50 mmol of the compound obtained in the preceding stage in 50 ml of dipropylamine are maintained at 150° C. for 10 hours. After cooling, the medium is concentrated under vacuum and the expected product is obtained after purification of the residue by chromatography on a column of silica, using a dichloromethane/ethanol/aqueous ammonia (90/10/1) mixture as eluent.

Stage C: 2-Hydroxymethyl-5-[2-(N,N-dipropylamino)ethoxy]-1,4-benzodioxane oxalate To a suspension containing 13.7 mmol of lithium aluminum hydride in 100 ml of ether, stirred at room temperature under a nitrogen atmosphere, is added dropwise a solution containing 12 mmol of the product obtained in the above stage in 50 ml of ether. The mixture is kept stirring for 1 hour and is hydrolyzed with saturated ammonium chloride solution. The organic phase is recovered, washed with water, dried and evaporated, and gives the expected product in the form of the base. To the latter, diluted in 50 ml of ethanol, is added 1 equivalent of oxalic acid, followed, after stirring for 5 minutes, by 50 ml of isopropyl ether. The oxalate is obtained by filtration and is dried. Melting point: 148° C.

EXAMPLE 11

5-[2-(2,3,4-Trimethoxybenzoylamino)ethoxy]-1,4-benzodioxane

Stage A: 5-Cyanomethoxy-1,4-benzodioxane

To a stirred suspension containing 0.38 mol of the compound obtained in Stage B of Example 1 and 1.14 mol of potassium carbonate in 500 ml of acetone is added dropwise a solution containing 0.76 mol of bromoacetonitrile in 100 ml of acetone. The medium is then kept stirring for 18 hours. After filtration of the salts and evaporation, the expected product is obtained.

Stage B: 5-(2-Aminoethoxy)-1,4-benzodioxane

The expected product is obtained according to the process described in Stage C of Example 10, from the product described in the above stage.

Stage C: 5-[2-(2,3,4-Trimethoxybenzoylamino)ethoxy]-1,4-benzodioxane

To a stirred solution, at room temperature, containing 4.7 mmol of the product obtained in the preceding stage in 20 ml of dichloromethane is added dropwise a solution containing 10.5 mmol of 3,4,5-trimethoxybenzoyl chloride in 20 ml of dichloromethane, followed by 10.5 mmol of triethylamine in 20 ml of dichloromethane. The mixture is then stirred at room temperature for 2 hours. After filtration of the salts and washing of the medium with water, the organic phase is dried and evaporated. The residue is taken up in ether and gives the expected product which precipitates and which is recrystallized in ethanol. Melting point: 128° C.

| | Elemental microanalysis: | | |
|---|---|---|---|
| | C % | H % | N % |
| calculated | 61.69 | 5.95 | 3.60 |
| found | 61.26 | 5.89 | 3.70 |

EXAMPLE 12

2-Hydroxymethyl-5-[2-(4-fluorobenzoylamino)ethoxy]-1,4-benzodioxane

Stage A: Ethyl ester of 5-cyanomethyl-1,4-benzodioxane-2-carboxylic acid

The expected product was obtained according to the process described in Stage A of Example 11, from the compound described in Stage A of Example 9 and bromoacetonitrile.

Stage B: 2-Hydroxymethyl-5-(2-aminoethoxy)-1,4-benzodioxane

The expected product was obtained according to the process described in Stage C of Example 10, from compound described in the above stage, using 2 equivalents of lithium aluminum hydride.

Stage C: 2-Hydroxymethyl-5-[2-(4-fluorobenzoylamino)ethoxy]-1,4-benzodioxane

The expected product was obtained according to the process described in Stage C of Example 11, from the compound described in the above stage and 4-fluorobenzoyl chloride. Melting point: 124° C.

| | Elemental microanalysis: | | |
|---|---|---|---|
| | C % | H % | N % |
| calculated | 62.24 | 5.22 | 4.03 |
| found | 62.13 | 5.30 | 3.88 |

EXAMPLE 13

5-[2-(3,4,5-Trimethoxybenzylamino)ethoxy-1,4-benzodioxane hydrochloride 6.3 mmol of the compound obtained in Stage C of Example 11 and 19 mmol of tetrabutylammonium borohydride are maintained at reflux in 100 ml of dichloromethane for 24 hours. After evaporation of the solvent, the reaction medium is hydrolyzed with 50 ml of 10% hydrochloric acid at room temperature. The mixture is then maintained at reflux for one hour. After extraction with dichloromethane, the organic phase is washed with sodium hydroxide, dried and concentrated under vacuum. The expected product, in the form of the base, is then obtained after purification of the residue by chromatography on a column of silica, using a dichloromethane/methanol (97/3) mixture as eluent. After dilution in ether and stoichiometric addition of 6N hydrochloric ether, the corresponding hydrochloride is obtained. Melting point: 149° C.

| | Elemental microanalysis: | | | |
|---|---|---|---|---|
| | C % | H % | N % | Cl % |
| calculated | 58.32 | 6.36 | 3.40 | 8.61 |
| found | 58.02 | 6.35 | 3.45 | 8.44 |

EXAMPLE 14

5-{3-[3-(4-Fluorobenzoylmethyl)pyrrolidin-1-yl]propyl}-1,4-benzodioxane hydrochloride Stage A: Methyl ester of 3-(2,3-dihydroxyphenyl)propionic acid The expected product is obtained by catalytic hydrogenation in methanol, at room temperature and pressure, in the presence of 10% palladium on charcoal as catalyst, of the methyl ester of (2,3-dihydroxy-phenyl)cinnamic acid (obtained from 2,3-dihydroxybenzaldehyde according to the procedure described in J. Het. Chem., 26, 193, 1989).

Stage B: 3-(2,3-Dihydroxyphenyl)propanol

The expected product is obtained according to the process described in Stage C of Example 10, from the compound obtained in the above stage.

Stage C: 5-(3-Hydroxypropyl)-1,4-benzodioxane

The expected product is obtained according to the process described in Stage A of Example 1, from the compound obtained in the above stage.

Stage D: 5-(3-Bromopropyl)-1,4-benzodioxane

To a stirred solution, at 8° C., containing 36 mmol of the compound obtained in the preceding stage and 58.4 mmol of carbon tetrabromide in 150 ml of dimethylformamide are added portionwise 58.4 mmol of triphenylphosphine. The mixture is stirred at 8° C. for 2 hours and is then poured into 300 ml of ice-water. The medium is extracted with ether and the ether phase is dried and evaporated. The expected product is then obtained by purification of the residue by chromatography on a column of silica, using dichloromethane as eluent.

Stage E: 5-{3-[3-(4-Fluorobenzoylmethyl)pyrrolidin-1-yl] propyl}-1,4-benzodioxane hydrochloride The expected product is obtained according to the process described in Stage D of Example 1, from the compound obtained in the above stage and 3-(4-fluorobenzoylmethyl)pyrrolidine.

| | Elemental microanalysis: | | | |
|---|---|---|---|---|
| | C % | H % | N % | Cl % |
| calculated | 65.79 | 6.48 | 3.34 | 8.44 |
| found | 65.11 | 6.11 | 4.03 | 8.32 |

EXAMPLE 15

5-{2-[4-(4-Fluorobenzoyl)perhydroazepin-1-yl]ethoxy}-1,4-benzodioxane hydrochloride A mixture of 5 g of 5-(2-chloroethoxy)-1,4-benzodioxane, 7.8 g of 4-(4-fluorobenzoyl)perhydroazepine hydrobromide (described in Patent EP 389,352), 1 g of potassium iodide and 6.5 g of potassium carbonate in 100 ml of diethyl ketone is maintained at 100 C. for 24 hours. The inorganic salts are then filtered off and the filtrate is concentrated under vacuum. The residue is purified by chromatography on a column of silica, with a dichloromethane/methanol/aqueous ammonia (97/3/0.3) eluent mixture. The base obtained is salified with hydrochloric methanol in an acetone/ether mixture. Melting point: 106°–107° C.

| | Elemental microanalysis: | | | |
|---|---|---|---|---|
| | C % | H % | N % | Cl % |
| calculated | 63.37 | 6.24 | 3.21 | 8.13 |
| found | 63.01 | 6.13 | 2.98 | 7.94 |

Pharmacological Study of the Compounds of the Invention

EXAMPLE 16

Receptor profile of the compounds of the invention

The interaction of these compounds with various receptors was determined using standard binding studies as described by M. J. Millan et al. (J. Pharmacol. Exp. Ther., 268, 337–352, 1994 and Drug News & Perspectives, 5, 397–406, 1992). The receptor profile of the compounds of the invention is presented in the table below. The affinities of the compounds are expressed as pKi.

| | Receptor Profile (pKi) | | | | | |
|---|---|---|---|---|---|---|
| Examples | $D_1$ | $D_2$ | $5\text{-}HT_{1A}$ | $5\text{-}HT_{2A}$ | $5\text{-}HT_{2C}$ | $\alpha_1$ |
| ex. 2 | 6.60 | 7.36 | 8.31 | 8.40 | 8.10 | 8.61 |
| ex. 5 | 6.56 | 7.33 | 8.32 | 8.48 | 8.03 | 8.19 |
| ex. 6 | 6.69 | 7.27 | 8.44 | 8.62 | 8.18 | 8.93 |
| ex. 7 | NT | 7.27 | 8.77 | 7.66 | 7.03 | NT |
| ex. 8 | NT | 6.59 | 8.41 | 7.88 | 7.02 | NT |
| Haloperidol | 7.39 | 8.73 | 5.55 | 7.08 | 5.24 | 8.01 |
| Clozapine | 6.74 | 6.65 | 6.53 | 7.63 | 8.06 | 8.22 |

NT = not tested

EXAMPLE 17

Antipsychotic properties

Two well-established tests were used in order to determine the antipsychotic properties of the compounds of the invention, in which tests all of the antipsychotic agents are clinically active, as has been shown by A. Y. Deutch et al. (Schizophrenia Research, 4, 121–156, 1991) and A. A. Mengens et al. (J. Pharmacol. Exp. Ther., 260, 160–167, 1992):

verticalization inhibition induced by a dopaminergic agonist: apomorphine (according to the procedure described by P. Protais et al., Psychopharmacol., 50, 1–6, 1976), motor activity inhibition induced by amphetamine (which increases the release of catecholamines) according to the procedure described by A. A. Mengens, cited above.

An activity in these tests appears to reflect blocking of the mesolimbic dopaminergic pathways, which are believed to be hyperactive in schizophrenics, as described by P. C. Waldmeier et al. (Eur. J. Pharmacol., 55, 363–373, 1979) and A. Y. Deutch, cited above. The activities of the compounds of the invention were compared with those of haloperidol and of clozapine.

Verticalization Test using Apomorphine in Mice

The experiment was performed on male CF (Charles River) mice of average weight 25 g. thirty minutes before the start of the test, each mouse was placed in a cylindrical cage (Ø12 cm 14 cm), with vertical metal bars and a smooth plastic lid, after having received a subcutaneous injection of solvent or of product. At $T_0$, a solution of apomorphine (0.75 mg/kg) or of physiological saline was administered subcutaneously to the animal, which was returned to the barred cage. At $T_{10}$ (10 minutes) and at $T_{20}$ (20 minutes), a score was attributed to each animal after observation for approximately one minute:

score 0 (4 feet on the floor);

score 1 (animal raised on hind legs, forefeet on the vertical bars);

score 2 (animal gripping on to the bars with all 4 feet).

The total score of the 2 measurements then represents the verticalization value of the animal, which is used for the statistical analysis.

Test of the Motor Activity Induced by Amphetamine

Male Wistar rats (200–220 g) were placed in transparent polycarbonate individual cages the night before the test. The locomotor activity was recorded using photoelectric cells (Système Lablinc, Coulbourn) connected via an interface to a microcomputer. There are two transverse banks of photoelectric cells per cage. The test takes place under artificial light, starting from 1.00 p.m., during daylight hours. The product or solvent was administered to the animal subcutaneously, 30 minutes before the start of the test. At $T_0$, the animal received an intraperitoneal injection of physiological saline or of D-amphetamine (2.5 mg/kg): the motor activity of the animal (small and large movements) was recorded continuously for 1 hour, from $T_0$ to $T_{60}$.

The results of these two tests are presented in the table below:

| Examples | Verticalization (Apomorphine) | | Locomotion (Amphetamine) | |
|---|---|---|---|---|
| | $DI_{50}$ (mg/kg) | (95% L.C.) (mg/kg) | $DI_{50}$ (mg/kg) | (95% L.C.) (mg/kg) |
| Ex. 2 | 0.28 | (0.17–0.47) | 2.17 | (1.44–3.28) |
| Ex. 5 | 0.26 | (0.12–0.57) | 2.80 | (1.51–5.18) |
| Ex. 6 | 0.25 | (0.15–0.41) | 1.94 | (1.05–3.60) |
| Ex. 7 | 0.41 | (0.04–3.99) | NT | |
| Ex. 8 (*) | ≈0.63 | | NT | |
| Haloperidol | 0.013 | (0.008–0.022) | 0.043 | (0.03–0.06) |
| Clozapine | 2.22 | (1.70–2.90) | 12.85 | (9.25–17.86) |

$ID_{50}$ (95% C.L.) = Inhibitory $Dose_{50}$ (95% Confidence Limits)
NT = not tested
(*) The precise value could not be determined

EXAMPLE 18

Catalepsy in rats

In order to determine the potential of the compounds of the invention to generate a syndrome of extrapyramidal type, the capacity to induce a catalepsy in rats was examined. This phenomenon is due to an antagonism of the nigrostriatal dopaminergic transmission. The activities of the compounds were compared with those of haloperidol and clozapine.

Procedure

Male Wistar rats (220–240 g) were placed in individual cages and food was witheld the night before the test. The test used to evaluate the cataleptogenic properties of a product consists in placing each of the animal's hind feet on the forefoot located on the same side and in measuring the time in seconds for which the animal kept this "crossed feet" position, up to 30 seconds, as described by P. C. Waldmeier et al. (Eur. J. Pharmacol., 55,363–373, 1979). Each animal underwent three tests, at intervals of one minute; the average value of the three tests then represents the catalepsy time of the animal, which is used for the statistical analysis. The product to be tested was administered to the animal subcutaneously, 30 minutes before the test.

The results of the induction of catalepsy in rats are presented in the table below.

The effective cataleptogenic dose $ED_{50}$ is that which induces catalepsy for an average duration of 15 seconds, that is to say for 50% of the maximum duration of the test (30 seconds).

| | Induction of the catalepsy | |
|---|---|---|
| Examples | $DE_{50}$ (mg/kg) | (95% C.L.) (mg/kg) |
| Ex. 2 | >40.0 | |
| Ex. 5 | >40.0 | |
| Ex. 6 | >40.0 | |
| Haloperidol | 0.156 | (0.05–0.38) |
| Clozapine | >40.0 | |

$ED_{50}$ (95% L.C.) = Effective $Dose_{50}$ (95% Confidence Limits)

EXAMPLE 19

Pharmaceutical composition
Preparation formula for 1000 tablets containing a 0.1 mg dose

| Compound of Example 2 | 100 mg |
|---|---|
| Hydroxypropylcellulose | 2 g |
| Wheat starch | 10 g |
| Lactose | 100 g |
| Magnesium stearate | 3 g |
| Talc | 3 g |

We claim:
1. A compound of formula (I):

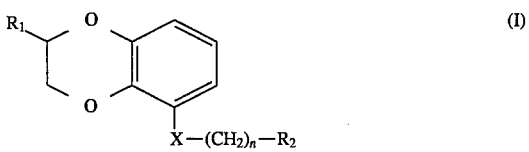

in which:
X represents oxygen or methylene,
n represents 1, 2 or 3,
$R_1$ represents hydrogen, aminocarbonyl or hydroxymethyl,
$R_2$ represents:

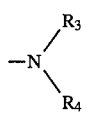

in which:
either $R_3$ represents hydrogen or linear or branched ($C_1$–$C_6$) alkyl, and $R_4$ represents:
linear or branched ($C_1$–$C_4$) alkyl
which is unsubstituted or substituted with phenyl (which is unsubstituted or substituted with one or more halogen or linear or branched ($C_1$–$C_4$) alkyl, linear or branched ($C_1$–$C_4$) alkoxy, trihalomethyl or hydroxyl), on condition that, in these cases, $R_1$ is other than hydrogen,
or which is substituted with benzoylamino (which is unsubstituted or substituted on the phenyl ring with one or more halogen or linear or branched ($C_1$–$C_4$) alkyl, linear or branched ($C_1$–$C_4$) alkoxy, trihalomethyl or hydroxyl),
or benzoyl (which is unsubstituted or substituted with one or more halogen or linear or branched ($C_1C_4$) alkyl, linear or branched ($C_1$–$C_4$) alkoxy, trihalomethyl or hydroxyl),
or $R_3$ and $R_4$ form, together with the nitrogen to which they are attached:

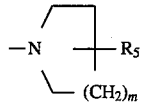

in which
m represents 1, 2 or 3,
$R_5$ represents benzoyl (which is unsubstituted or substituted with one or more halogen or linear or branched ($C_1$–$C_4$) alkyl, linear or branched ($C_1$–$C_4$) alkoxy, hydroxyl or trihalomethyl),
benzoylmethyl (which is unsubstituted or substituted on the phenyl ring with one or more halogen or linear or branched ($C_1$–$C_4$) alkyl, linear or branched ($C_1$–$C_4$) alkoxy, hydroxyl or trihalomethyl), 2-oxo-(3H)-benzimidazol-1-yl, 1H-indazol-3-yl methyl (which is unsubstituted or substituted on the phenyl ring with halogen), or 1,2-benzisoxazol-3-yl methyl (which is unsubstituted or substituted on the phenyl ring with halogen), an enantiomer, diastereoisomer or epimer thereof, or an addition salt thereof with a pharmaceutically-acceptable acid or base.

2. A compound of claim 1, in which X represents oxygen, an enantiomer, diastereoisomer or epimer thereof, or an addition salt thereof with a pharmaceutically-acceptable acid or base.

3. A compound of claim 1, in which X represents methylene, an enantiomer, diastereoisomer or epimer thereof, or an addition salt thereof with a pharmaceutically-acceptable acid or base.

4. A compound of claim 1, in which X represents oxygen and $R_1$ represents hydrogen, an enantiomer, diastereoisomer or epimer thereof, or an addition salt thereof with a pharmaceutically-acceptable acid or base.

5. A compound of claim 1, in which $R_3$ and $R_4$ form, together with the nitrogen atom to which they are attached, a group:

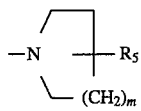

in which m and $R_5$ are as defined in claim 1, an enantiomer, diastereoisomer or epimer thereof, or an addition salt thereof with a pharmaceutically-acceptable acid or base.

6. A compound of claim 1 which is 5-{2-[3-(4-fluorobenzoylmethyl)pyrrolidin-1-yl]ethoxy}-1,4-benzodioxane, an enantiomer thereof, or an addition salt thereof with a pharmaceutically-acceptable acid.

7. A method for treating a mammal afflicted with schizophrenia comprising the step of administering to the mammal an amount of a compound of claim 1 which is effective for alleviation of said condition.

8. A pharmaceutical composition useful in treating schizophrenia comprising as active principle an effective amount of a compound as claimed in claim 1, together with one or more pharmaceutically-acceptable excipients or vehicles.

* * * * *

UNITED STATES PATENT AND TRADEMARK OFFICE
CERTIFICATE OF CORRECTION

PATENT NO. : 5,500,443
DATED : Mar. 19, 1996
INVENTOR(S) : Gilbert Lavielle, Patrick Hautefaye, Olivier Muller, Mark Millan, Mauricette Brocco It is certified that error appears in the above-indentified patent and that said Letters Patent is hereby corrected as shown below:

Column 12, line 25: Insert a -- ] -- at the end of the line.  Pg. 15, line 17

Column 12, line 26: Delete the "]" at the beginning of the line.

Column 13, line 24: Delete the "-" (dash) at the end of the line.  Pg. 16, line 27

Column 13, line 25: Insert a _dash_ at the beginning of the line.  Pg. 16, line 28

Column 20, line 59: "in which" should read -- in which: --.  Pg. 27, line 26

Signed and Sealed this

Eighteenth Day of June, 1996

Attest:

BRUCE LEHMAN

*Attesting Officer*          *Commissioner of Patents and Trademarks*